US008844050B1

(12) United States Patent
Miasnik et al.

(10) Patent No.: US 8,844,050 B1
(45) Date of Patent: Sep. 23, 2014

(54) PERSONNEL CRISIS COMMUNICATIONS MANAGEMENT AND PERSONNEL STATUS TRACKING SYSTEM

(71) Applicant: AtHoc, Inc., San Mateo, CA (US)

(72) Inventors: Guy Miasnik, Mountain View, CA (US); Aviv Siegel, San Mateo, CA (US); Rakesh Gupta, Sunnyvale, CA (US)

(73) Assignee: AtHoc, Inc., San Mateo, CA (US)

( * ) Notice: Subject to any disclaimer, the term of this patent is extended or adjusted under 35 U.S.C. 154(b) by 0 days.

(21) Appl. No.: 14/197,535

(22) Filed: Mar. 5, 2014

Related U.S. Application Data

(60) Provisional application No. 61/798,825, filed on Mar. 15, 2013.

(51) Int. Cl.
*H04L 29/06* (2006.01)
*H04N 21/25* (2011.01)
*G06F 17/30* (2006.01)
*G06F 19/00* (2011.01)

(52) U.S. Cl.
CPC .......... *G06F 17/30861* (2013.01); *H04L 63/08* (2013.01); *H04N 21/252* (2013.01); *G06F 19/34* (2013.01)
USPC .......................................................... 726/26

(58) Field of Classification Search
CPC ............................. H02N 21/252; G06F 19/34
USPC .......................................................... 726/26
See application file for complete search history.

(56) References Cited

U.S. PATENT DOCUMENTS

| 6,158,903 | A  | * | 12/2000 | Schaeffer et al. | ............. 709/204 |
| 7,301,450 | B2 |   | 11/2007 | Carrino | |
| 7,973,655 | B2 | * | 7/2011  | Blinnikka et al. | ....... 340/539.13 |
| 2005/0091368 | A1 | | 4/2005 | Ozburn | |
| 2010/0069115 | A1 | * | 3/2010 | Liu | ............................ 455/556.1 |
| 2011/0095881 | A1 | | 4/2011 | Rosentel et al. | |
| 2011/0260833 | A1 | | 10/2011 | Lemmon | |
| 2012/0226526 | A1 | | 9/2012 | Donovan et al. | |

OTHER PUBLICATIONS

PCT International Search Report and Written Opinion for PCT/US2014/021556, Jun. 27, 2014, 20 Pages.

* cited by examiner

*Primary Examiner* — Pramila Parthasarathy
*Assistant Examiner* — Dao Ho
(74) *Attorney, Agent, or Firm* — Fenwick & West LLP

(57) ABSTRACT

Systems and methods are disclosed for providing personnel communications management within an enterprise or group of related enterprises during crisis situations. In particular, the systems and methods provide event management, shared situational awareness, personnel status tracking, and unified crisis notification management to multiple users.

23 Claims, 13 Drawing Sheets

PERSONNEL CRISIS COMMUNICATIONS MANAGEMENT AND PERSONNEL STATUS TRACKING SYSTEM

CROSS REFERENCE TO RELATED APPLICATIONS

This application claims the benefit of U.S. Provisional Patent Application Ser. No. 61/798,825, filed Mar. 15, 2013, entitled "Personnel Crisis Communications Management System," which is incorporated by reference in its entirety as if fully set forth herein.

BACKGROUND

The subject matter described herein relates to crisis management, and in particular, information proliferation to and from personnel and other individuals associated with an enterprise.

Over the past decade, occurrences of both man-made and natural disasters (e.g. nuclear incidents, shootings, earthquakes, hurricanes, fires, and more) have resulted in significant loss of life, injuries and damaged property. Local, regional and national first responders as well as emergency management officials have been challenged to respond quickly and effectively, while communicating with multiple organizations, government agencies, emergency management personnel and individuals in the affected areas. This challenge has been compounded by the difficulty inherent in synchronizing disparate and incompatible communications and emergency management systems, thus causing significant delays in crisis management and response.

It was through these disasters and response experiences that multiple needs were identified. Among these needs are a need for rich and rapid crisis communications tools, a need to develop a common understanding of a crisis situation using various data sources (including the general populace), a need for dissemination of relevant actionable information and instructions to the impacted personnel in real time, and a need for large scale tracking of personnel status and location throughout a crisis.

As these needs emerged, so did advancements in technology. With new communications technologies and the ubiquitous, omnipresent Internet Protocol ("IP") infrastructure, Emergency Mass Notification System (EMNS) providers now provide single button, unified alerting to facility-based devices (e.g., fire alarms, public address systems, Giant Voice, etc.) and personal devices (e.g., via phone calls, text messaging, email, computer pop-ups, etc.). Current EMNS systems use a variety of channels and formats for outbound communications (from an operations center) to affected personnel, as well as collecting and tracking solicited responses.

While emergency notification is focused on outbound communication, the lessons learned from disasters point to the need for collecting inbound reports (from crisis locations and their vicinities) as well. For example, reporting a shooting in a school, a flooded area, a wild fire, or a terrorist activity. The recent public service campaign of "See Something, Say Something" from the US Dept. of Homeland Security, and "Every Soldier is a sensor" initiative within the US Dept. of Defense are examples of the philosophy that collecting, analyzing and acting upon inbound information is essential for effective crisis situation handling.

Until recently, 911 communications, the primary source for such inbound information, was inadequate for capturing rich content. The scope of 911 communications was extended to adopt newer technologies via the Next Generation 911 initiative (NG911). Implementation of NG911 now enables communication flow via the IP network, which also enables newer and more advanced capabilities that support rich communication from the public to the Public Safety Answering Points (PSAPs).

SUMMARY

Systems and methods are disclosed for communications management for personnel within (and people associated with) an enterprise or group of related enterprises during crisis events, as well as computer readable storage mediums storing instructions for performing such methods. Various embodiments provide some or all of: shared situational awareness, inbound event management, unified crisis notification, personnel status reporting, and personnel location tracking. Integration of these features within a single system infrastructure enables increased efficiency of crisis event management as compared to using multiple, distinct systems. This provides, for example, more efficient response to crisis events, fewer casualties, and minimization of property damage.

The disclosed systems and methods extend the reach and flow of situational awareness and rich multi-modal communications beyond an operations center or Command and Control Center to all enterprise constituents, organizations and individuals, thereby enabling the organization to effectively act in an informed, efficient and expeditious manner.

In one embodiment, reliable and traceable communication management methods are used, for example, in life-safety applications where reliable information regarding message delivery is of paramount importance. In at least one embodiment, an enterprise's existing communications, network and data infrastructures are utilized for crisis event communications management, further increasing the overall efficiency of the crisis management process.

One example embodiment of a system and method for personnel crisis communications management includes the following 6 features:

1. A Crisis Communications Management Platform, managing multi-directional, multi-modal communications amongst enterprise personnel and other related personnel during crisis events as well as during routine enterprise operations.

2. Enterprise-level design, supporting various types of constituents of enterprise communications, providing each constituent type with type-appropriate views and communications channels. Constituent types include, but are not limited to, emergency management personnel, emergency first responders, incident commanders, enterprise management personnel, members of the enterprise, and individuals related to members of the enterprise.

3. Integration of crucial crisis-management functionalities within a single platform, including all capabilities, specifically inbound event management, shared situational awareness, unified notification, personnel status reporting, and personnel location tracking.

4. Leverage of existing enterprise infrastructure including, but not limited to, computer network hardware and personnel databases. This leveraging results, amongst other benefits, in reduced costs of acquisition and maintenance for the enterprise.

5. Closed-loop, auditable, multi-directional, interactive and multi-modal communications methodologies resulting in communications reliability as required by life-safety systems.

6. Interconnecting multiple enterprises within a sphere of personnel safety, enhancing the coordination between various crisis management organizations typically required in real-life crisis.

Other embodiments include different and/or additional features to those outlined above.

BRIEF DESCRIPTION OF THE DRAWINGS

The figures depict various embodiments for purposes of illustration only. One skilled in the art will readily recognize from the following discussion that alternative embodiments of the illustrated systems and methods may be employed without departing from the principles described herein.

DETAILED DESCRIPTION

No system exists today that integrates all critical crisis communications management components into a single platform, including inbound reports processing, shared situational awareness, personnel tracking and outbound mass notification. Existing operations center systems rely mostly on voice communication (radio, mobile and landline phones) for operational communication. Common operating picture exists within operations centers but it is not shared with personnel and others in the field and is not integrated with information received from the field—including media, first responders' locations, etc.

As described above, there is a need for timely and efficient crisis communications management to provide reliable, timely information to all individuals associated with an event who require it, without compromising the data security of the enterprises and other entities involved in the event. Inbound and outbound communication flows implemented on IP networks facilitate more effective ways to intercommunicate with the affected enterprise and emergency service personnel during a crisis situation. The enterprise could be a corporation, university campus, industrial facility, military base, military unit, local jurisdiction, or the like. The enterprise may be geographically bound to a certain location (e.g., a factory) or be geographically distributed (e.g., all of the offices of a multi-national corporation).

The widespread adoption of data communications devices such as smart phones provides significant opportunities to improve crisis management systems that are yet to be realized. These devices provide extended capabilities, including integrated geo-location awareness and multimedia support (e.g., media playing, capturing, and sharing) that can be used to assist enterprise and emergency personnel in reporting and responding efficiently to a crisis event. The value of such inbound reports is increased if they include and/or can be correlated with additional information describing the reported event, such as a photo or video of the event, the event's location, and/or information regarding the reporting individual. In some instances, information about the reporting individual is particularly valuable, as it can aid in confirming the validity, accuracy, and context of the received report.

System Deployment Architecture

Figure 1:
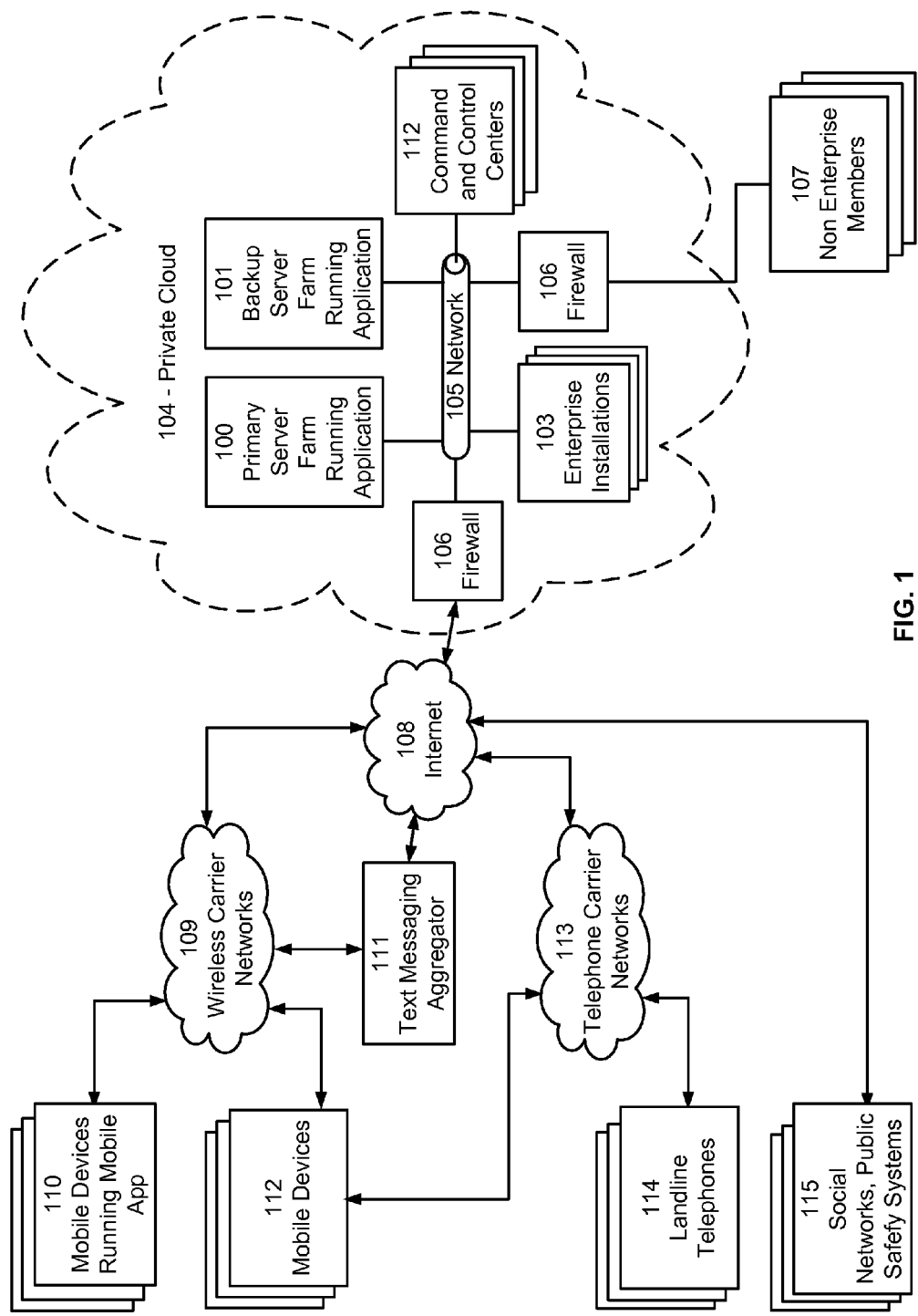
FIG. 1 is a high-level diagram illustrating a networked system for providing crisis communications management for an enterprise or group of enterprises, according to one embodiment.

FIG. 1 shows a networked system for providing personnel crisis communications management for an enterprise or group of enterprises, according to one embodiment. A personnel crisis communications management application is deployed on one or more primary server farms 100. Each farm contains one or more servers which act in unison to provide users with high availability, secure and scalable functionality. Any number of server farms can act as backup farms 101, typically located at sites where failures such as network and power outages are independent of failures at the primary farms.

In one embodiment, the application is deployed on the enterprise's premises, behind a firewall 106 and can be integrated securely with user directory databases, internal resources such as networks, telephone PBXs, in-building and "Giant Voice" alerting systems, physical security sensors, and the like. In another embodiment, the application is provided as software as a service (SaaS) in a Cloud configuration. Hybrid solutions with some aspects of the application located on-site and others accessed from the cloud can also be configured. In other embodiments, specialized hardware configured to provide some or all of the functionality described herein is deployed on the enterprise's premises.

One or more operations centers or Command and Control Centers 102 enable system operators and administrators to control all of the system's functionality using off-the-shelf computers or mobile devices running web browsers connected to the network directly or via a Virtual Private Network (VPN). In some embodiments, specialized display and control systems, such as large touch-sensitive screens, are installed in Command and Control centers 102 to enable operators to efficiently view and interact with a shared situational awareness display.

One or more Enterprise Campuses or Installations 103 contain systems and devices running the system's applications. These installations, which are described in more detail with reference to FIG. 2, enable users to be notified of an event and directed to act and respond to instructions provided by the system. Similarly, non-enterprise members 107 that may be hosted by the enterprise campus, or be remote, are provided with the same functionality. The types of non-enterprise members 107 that are included in the system are dependent on the nature of the enterprise. For example, such non-enterprise members can include tenant units on a military installation, family members and dependents of service members, guests on a university campus, contractors working for a corporation, and the like.

The server farms 100 and 101, Command and Control Centers 102, and Enterprise Installations 103, as well as the enterprise's off-the-shelf network 105 operate within the enterprise's Private Cloud 105, which is protected from the Internet by the enterprise's firewall 106. Non-enterprise members 107 may be served by the same private cloud 105 or by a separate network (public or private), protected by a firewall 106.

The system can also communicate with member and non-member constituents of the enterprise through the Internet 108. Mobile devices such as tablet computers and smart phones, running a mobile application 110, communicate with the system through their respective wireless carrier networks 109. Other mobile devices such as mobile phones and pagers communicate through either their respective wireless 109 or landline 113 carrier networks. Text message aggregators 111 can be used by the system to send messages to all types of mobile devices using the Short Messaging Service (SMS) protocol. In one embodiment, the system can also receive SMS messages from text message aggregators 111 and/or directly from mobile devices 112. Landline telephone devices 114 can communicate with the system though their respective telephone carrier networks. In other embodiments, the system communicates with constituents using additional and/or different devices and communications networks, including specialized, custom built communications devices and/or network infrastructures.

In one embodiment, the system also communicates with constituents through the Internet 108 via social networks such as FACEBOOK and TWITTER and/or sends alerts through public safety systems such as the Emergency Alerting Service (EAS) and the Integrated Public Alert & Warning System (IPAWS).

Figure 2:
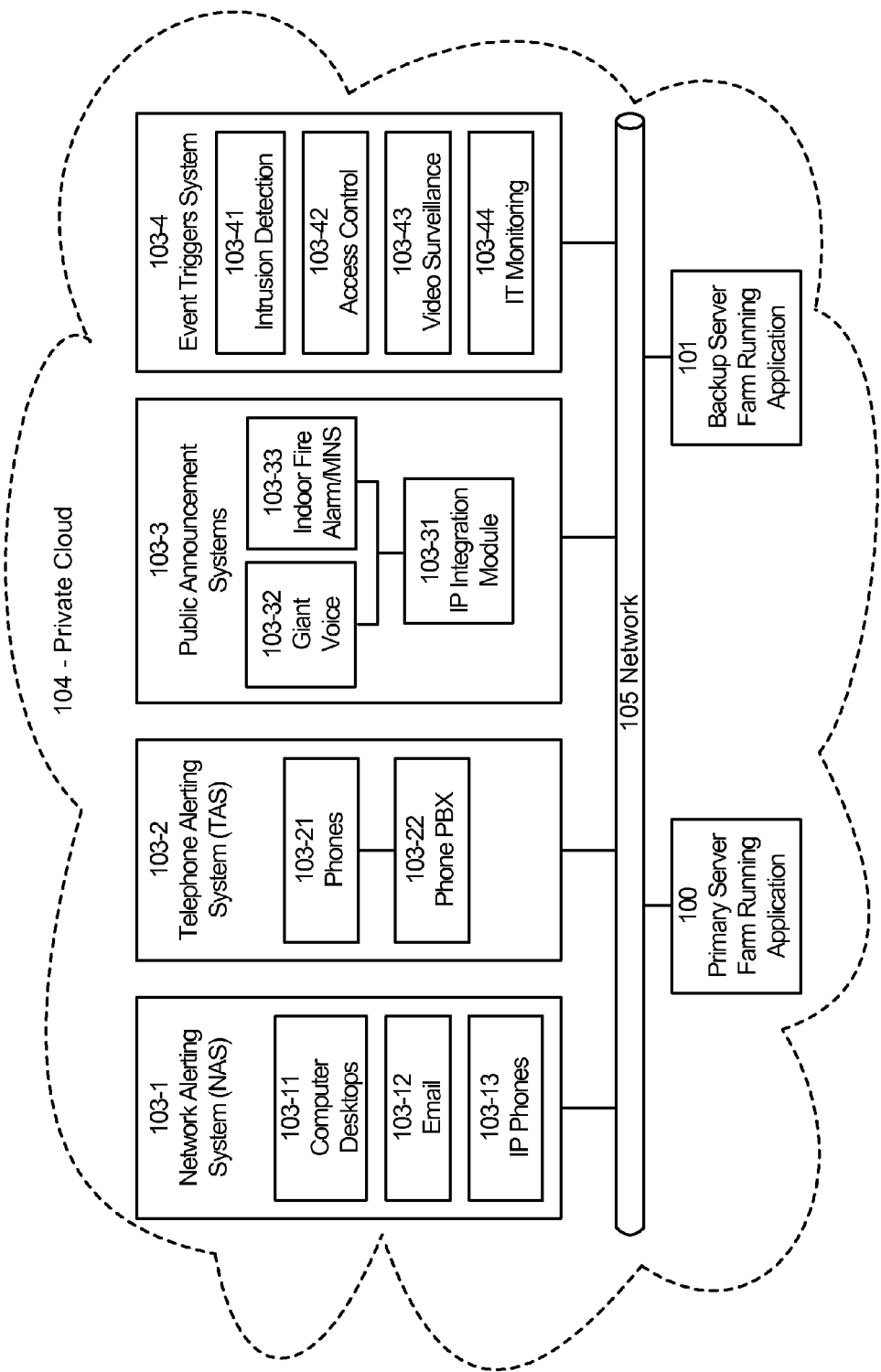
FIG. 2 is a high-level diagram illustrating the configuration of an enterprise network, according to one embodiment.

FIG. 2 illustrates the configuration of the portion of the wider network shown in FIG. 1 that is within the enterprise's private cloud 104, according to one embodiment. The embodiment shown utilizes the enterprise's existing IP network 105. The enterprise's private cloud 104 provides a high security environment for the system to operate within.

In the embodiment shown, the portion of the network within the enterprise's private cloud 104 includes a network alerting system (NAS) 103-1, a telephone alerting system (TAS) 103-2, a public announcement system 103-3, and an event triggers system 103-4. A typical deployment also includes one or more servers running the application 100 and an off-the-shelf database management system. Alternatively, a custom designed database management system can be used. When more than one server is deployed, they can be configured as a "server farm" with load balancing providing for high performance, scalable operation. The deployment can also include a hot backup server farm 101.

The NAS 103-1 includes computer popup alerting applications running on desktop or laptop computers throughout the enterprise 103-11 that provide the capabilities of bi-directional communications with the enterprise's office-based personnel. Members of the enterprise can also communicate bi-directionally with the system using an enterprise email system 103-12 and/or an IP-based phone system 103-13.

The Telephone Alerting System (TAS) 103-2 interfaces the system with the enterprise's non-IP telephones 103-21 through the enterprise's Private Branch Exchange (PBX) 103-22. In one embodiment, the TAS 103-2 is also used to provide notifications to constituents outside of the enterprise's private cloud 104. For example, in the case of a crisis event, the TAS 103-2 may make an automated telephone call to the home phone number or mobile phone of one or more constituents.

The enterprise's public announcement systems 103-3 can be interfaced to the system through an IP Integration Module 103-31. Such public announcement systems include, but are not limited to, off-the shelf Giant Voice 103-32 systems for outdoor notification and Indoor Fire Alarm/Mass Notifications Systems 103-33 for in-building notifications.

The event triggers system 103-4 provides event inputs to the application that are used to identify when crisis events are occurring. In the embodiment shown, the event triggers system 103-4 includes an intrusion detection system 103-41, an access control system 103-42, a video surveillance system 103-43, and an IT monitoring system 103-44. In other embodiments, the event triggers system 103-4 includes different and/or additional systems, such as systems that monitor temperature, humidity, industrial equipment operating parameters, and the like.

Figure 3A:
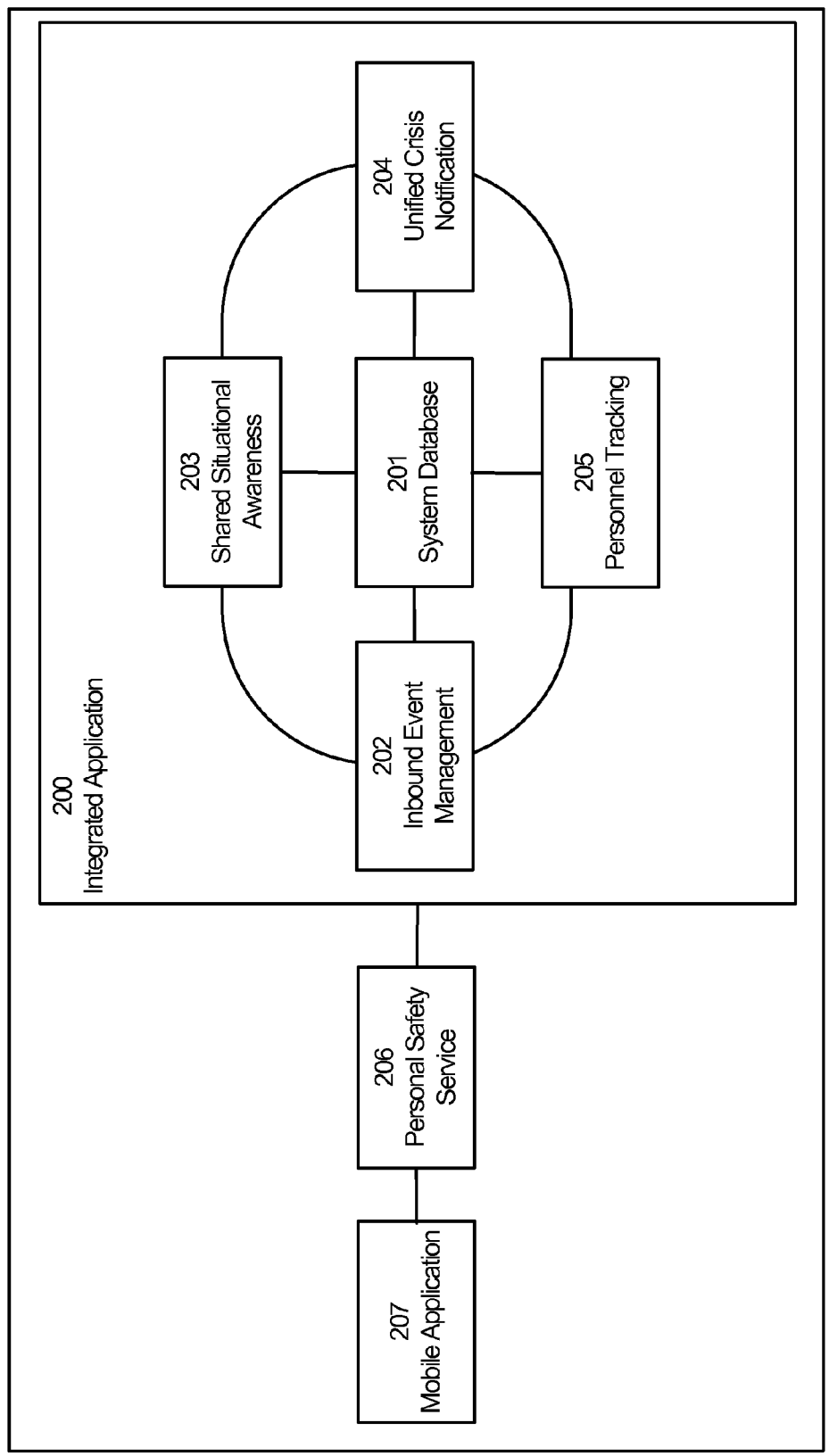
FIG. 3A is a high-level diagram illustrating the components of an integrated application for providing crisis communications management for an enterprise or group of enterprises, according to one embodiment.

FIG. 3A is a high-level diagram illustrating the components of an integrated application 200 for providing crisis communications management for an enterprise or group of enterprises, according to one embodiment. In the embodiment shown, the integrated application 200 includes subsystems for providing inbound event management 202, shared situational awareness 203, unified crisis notification management 204, and personnel tracking 205.

In addition to the integrated application 200, some embodiments include mobile applications 207 used by mobile users with devices such as smart phones or tablet computers that are interfaced to the integrated application though a personal safety service (PSS) 206. This service can run on any server or server farm on the Internet (or otherwise connected to instances of the mobile application 207 and the integrated application 200) and can serve one or more enterprise integrated applications 200. In one embodiment, the PSS 206 serves as an interface that connects the mobile application 207 running on a device (e.g., a smart phone) connected to a public network 108 to the integrated application hosted on a system within the enterprise's private network 104, without compromising the security of the private network.

Figure 3B:
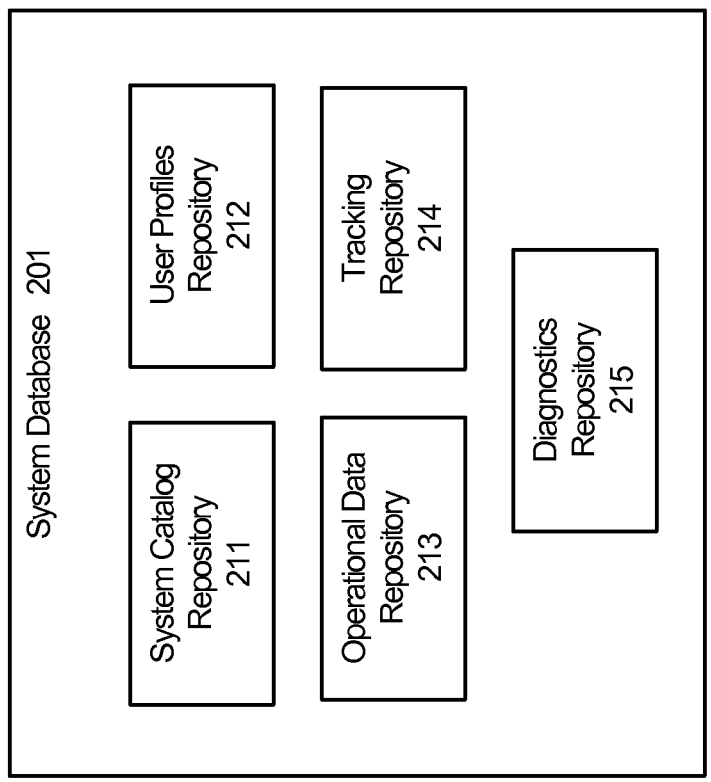
FIG. 3B is a high-level diagram illustrating the components of the system database shown in FIG. 3A, according to one embodiment.

The integrated application's functionality is supported by a system database 201 (e.g., a database management system), which incorporates several logical persistent repositories. In one embodiment, as illustrated in FIG. 3B, the system database 201 includes a system catalog repository 211, a user profiles repository 212, an operational data repository 213, a tracking repository 214, and a diagnostics repository 215.

The system catalog repository 211 contains system configuration and setup data. In one embodiment, the system catalog repository 211 includes a catalog of alert scenarios, visual and audio template libraries, custom attributes configurations, organizational hierarchies, device and delivery configurations, integration agent configurations, operator roles and permissions, event configurations, business rules, and static map layers. This data is setup by a system installer and is maintained by system administrators and operators. In other embodiments, the system catalog repository 211 contains additional and/or different data.

The user profiles repository 212 contains user profiles and corresponding data. In one embodiment, the user profiles repository 212 includes user attributes, contact details, and delivery preferences. The user profiles data can be synchronized with external personnel data repositories (such as Active Directory or LDAP). A web-based System Management password-protected module is provided for system administrators for managing this synchronization. A web and mobile based self-service password-protected module can also be provided for end-users to register and update their own profile information. In other embodiments, the user profile repository 212 contains additional and/or different data.

The operational data repository 213 contains the operational data, including published alert messages along with corresponding targeting and recipient lists. In various embodiments, the operational data repository 213 also contains additional and/or different data, such as geographic layers, incoming events, incoming media, activity logs, etc.

The tracking repository 214 contains tracking events data, such as alert delivery events (e.g., notifications that a message has been successfully sent, received, and responded to). In various embodiments, the tracking repository 214 also contains personnel tracking events, check-in/check-out notifiers, and the like.

The diagnostics repository 215 contains a running centralized system events log, capturing application level events categorized by event source and severity. In one embodiment, the diagnostics repository 215 is optimized for high throughput. In one embodiment, the diagnostics repository 215 also contains exceptions and application level log-data. The data in the diagnostics repository 215 can be used for system health monitoring, troubleshooting, and the like.

Figure 4:
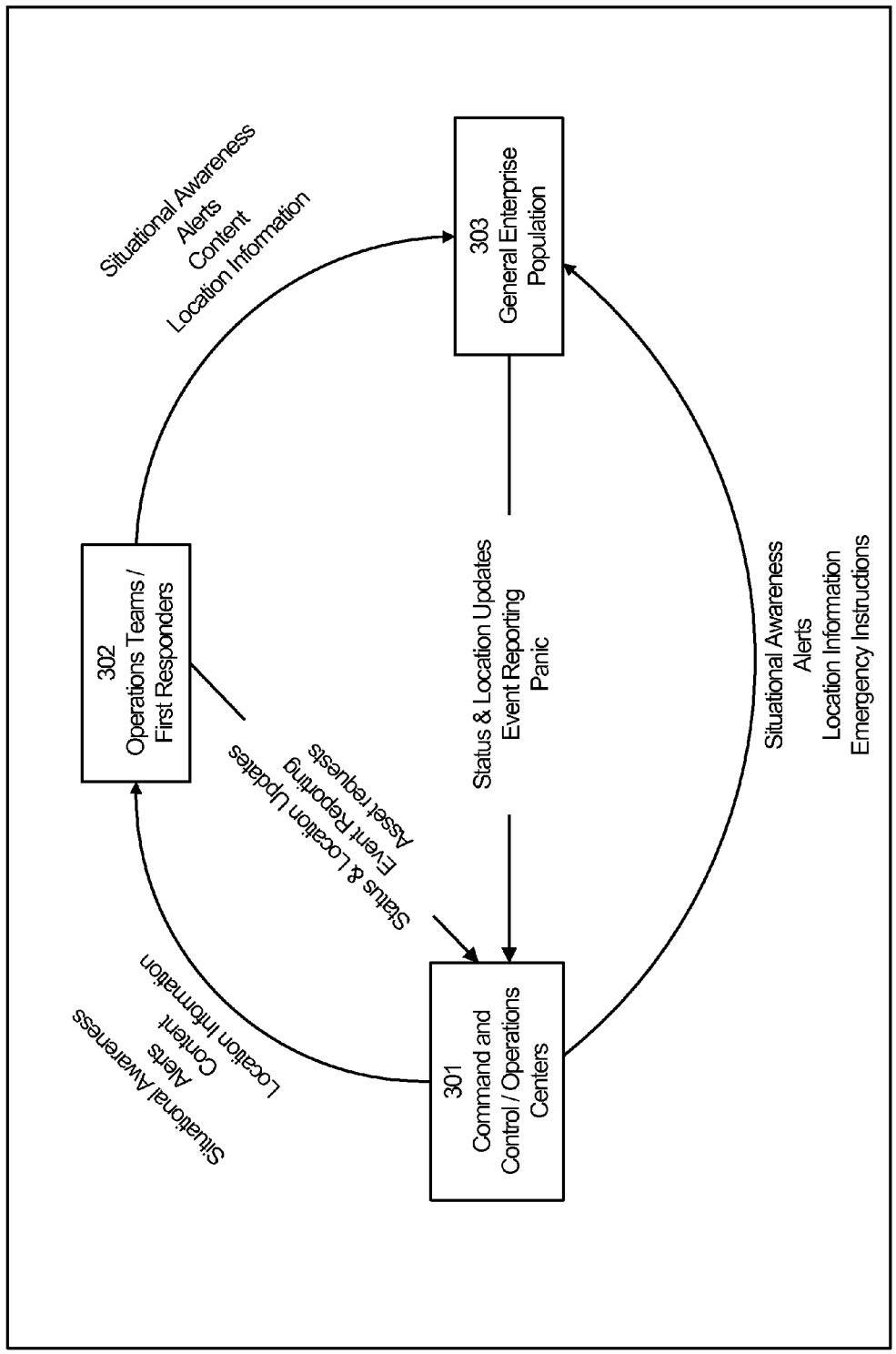
FIG. 4 is a diagram illustrating the exchange of information between various constituents, according to one embodiment.

FIG. 4 illustrates typical exchanges of various types of information amongst enterprise constituents involved in personnel communications during crisis events, according to one embodiment. Those constituents include, but are not limited to Command & Control Centers/Operations Centers 301, Operations Teams/First Responders 302, and General Population/Enterprise Members 303. The flow of situational awareness and response actions is extended to all constituents within an enterprise and to the general population, thereby enabling the enterprise and/or community to effectively act in an informed and expeditious manner.

During a crisis event it is critical to establish a flow of information between authorities, organizations and individuals and gain visibility into the ongoing crisis-related activities. In one embodiment, this is achieved by integrating bi-directional communication channels into the crisis management communication process by leveraging the ubiquitous mobile devices, mobile network, and smart-phones in use today. Several aspects of the system and method disclosed contribute to improved information flow during crisis situations.

A wide range of content, including alerts, support information, location information, event reports, field reports, emergency requests, help-me requests, personnel status, and personnel location can all be processed and distributed by a single integrated system. By using an integrated system, the reach of any given piece of content is expanded. All of the content within the system is potentially available to all of the constituents, in any location, as required, dependent on authorization under the role-based security and access permission protocols in place for the enterprise.

The integrated system also enables the general enterprise membership and/or the general population, as well as the emergency response teams, to report information and status back to the operations center and within smaller groups. This content can include multimedia data—enabling text, audio, image, and video information to be both provided by and delivered to any constituents associated with the enterprise, as required (and authorized).

Figure 5A:
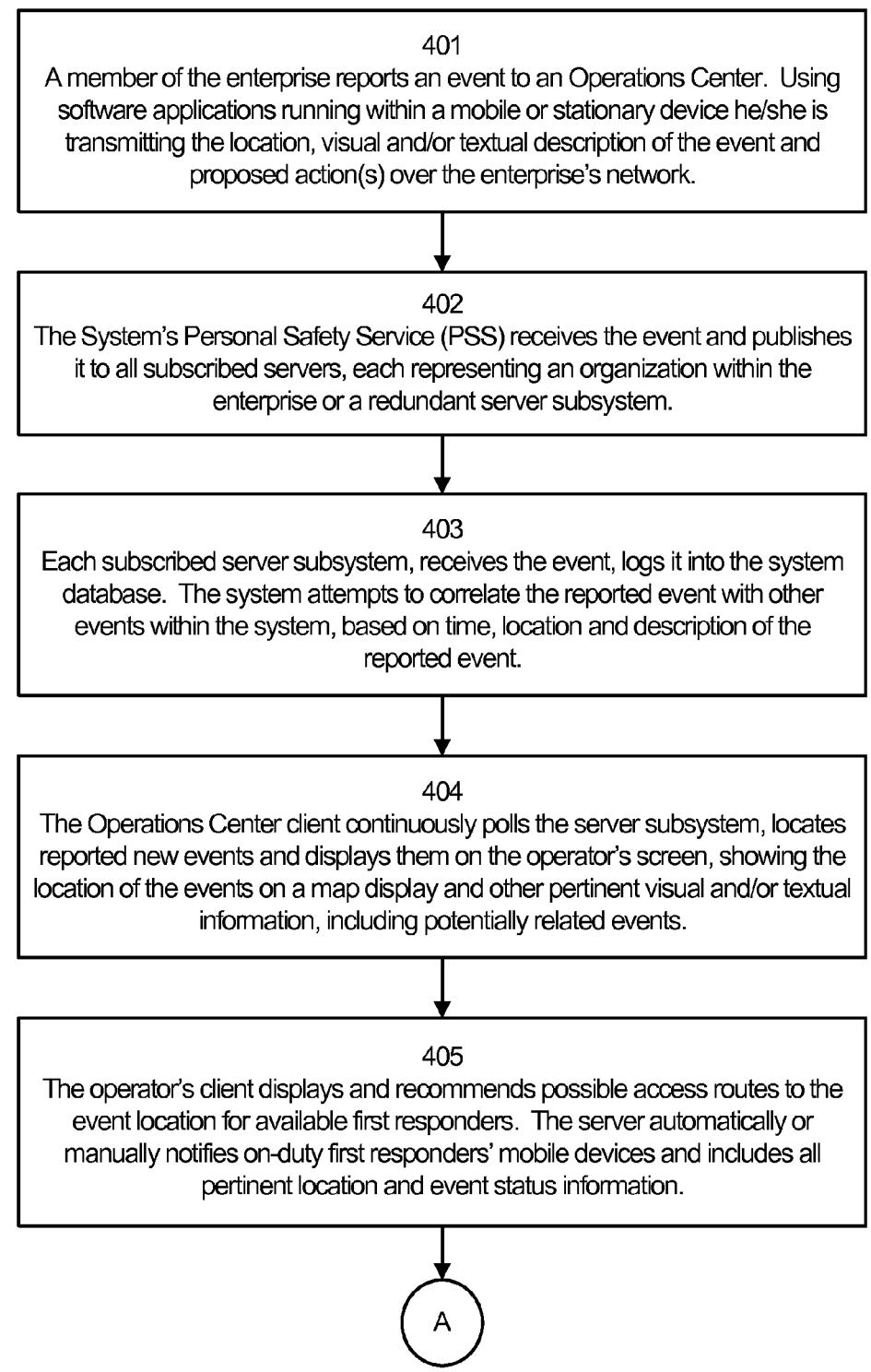
FIGS. 5A and 5B show a flow-chart illustrating a method for providing crisis communications management for an enterprise or group of enterprises, according to one embodiment.
Figure 5B:
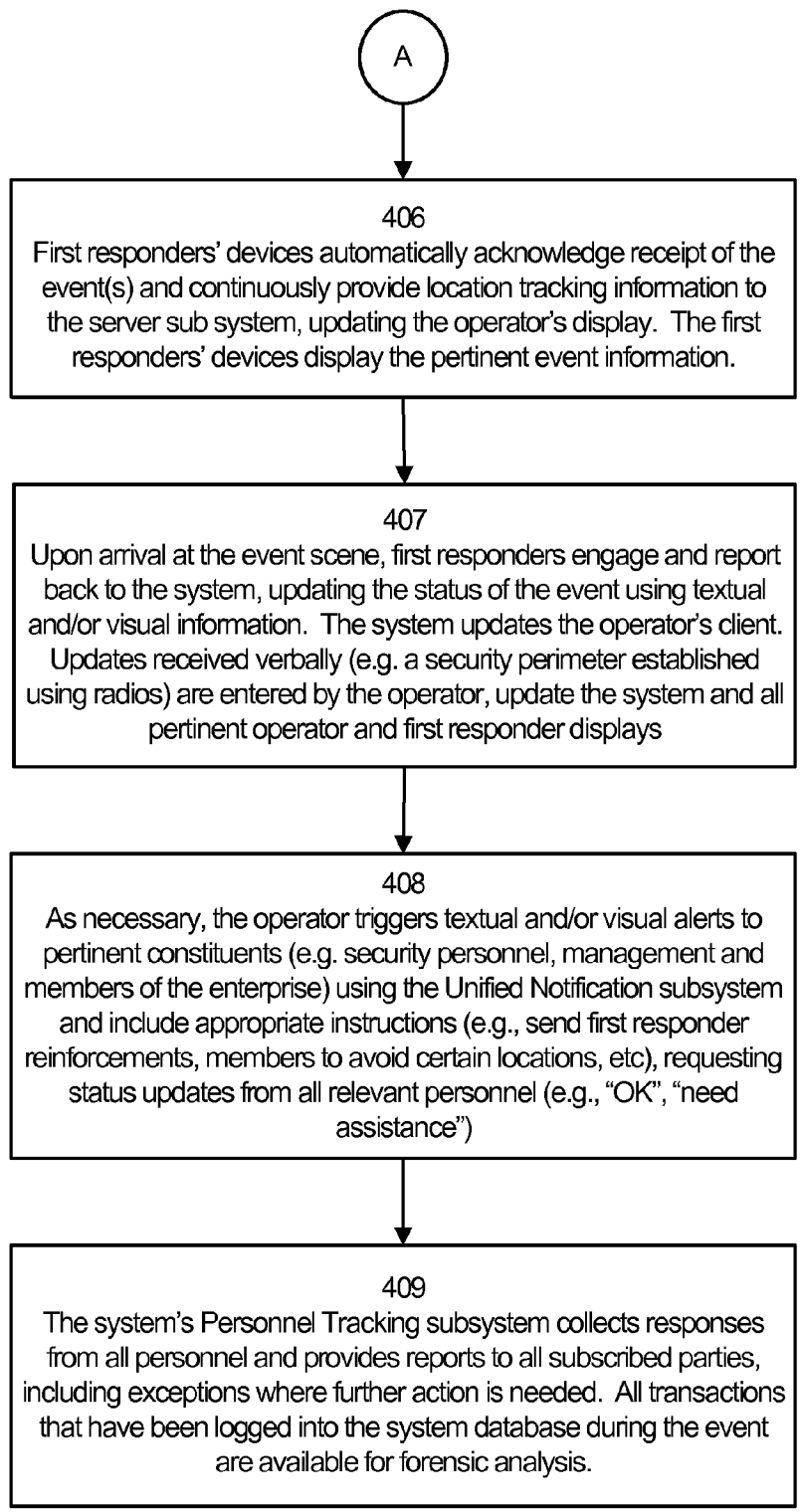

FIG. 5A and FIG. 5B illustrate a method for providing crisis communications management for an enterprise or group of enterprises using the hardware configuration illustrated in FIGS. 1-3, according to one embodiment. A member of the enterprise reports 401 an event to an Operations Center or Command and Control Center. Using software applications (e.g., mobile application 207) running within a mobile device 110 or a stationary device (not shown), the member transmits an event report over the enterprise's network 105 and/or the Internet 108. In embodiments that include a PSS 206, such as the one shown in FIG. 3A, the event report is transmitted via the PSS. In one embodiment, the event report includes the location, a visual and/or textual description of the event, and, optionally, proposed action(s) to be taken.

Assuming one is used, the system's PSS 206 receives 402 the event report and publishes it to all subscribed servers, each representing an organization within the enterprise or adjacent organizations. If a PSS 206 is not used, a dedicated routing module (not shown) can be used to publish the event report to all subscribing servers.

Each subscribed server subsystem, receives 403 the event report and logs it into the system database 201. In one embodiment, the system attempts to correlate the reported event with other events within the system, based on time, location and description of the reported event.

If the event report corresponds to a new event, the system notifies 404 the Operation Center operator. In one embodiment, the system displays the new event on the operator's screen, showing the location of the event on a map display and other pertinent visual and/or textual information, including potentially related events.

The operator analyzes the information and recommends 405 possible access routes to the event location for available first responders. In one embodiment, the operator recommends 405 possible access routes by outlining them on the map. The server automatically or manually (by operator activation) notifies on-duty first responders' mobile devices and includes all pertinent location and event status information.

The first responders' devices acknowledge 406 receipt of the event (either by requesting user confirmation or automatically) and continuously provide location tracking information back to the server subsystem, updating the Operation Center operator display. The first responders' devices display the pertinent event information, updated substantially in real-time.

Upon arrival at the event scene, first responders engage (e.g., check-in) and report back 407 to the system, updating the status of the event using textual and/or visual information. The system also updates the operator's client. Other enterprise and non-enterprise constituents, based on their role and corresponding access permissions may also receive some or all of the information updates. In one embodiment, updates received verbally (e.g., a security perimeter established using radios) are entered by the operator, thus updating the system and all pertinent operator and first responder displays. In another embodiment, verbal updates are processed automatically or semi-automatically. For example, the system may use a speech-to-text algorithm and present a recommended update to the operator for manual approval, thus reducing the amount of time the operator spends entering the update.

As necessary, the operator triggers 408 textual and/or visual alerts to pertinent constituents (e.g., security personnel, management, and members of the enterprise) using the unified crisis notification subsystem 204. In one embodiment, the alerts include appropriate instructions (e.g., send first responder reinforcements, members to avoid certain locations, etc.) and/or request a status update from all relevant personnel (e.g., "OK", "need assistance").

The system's personnel tracking subsystem 205 collects 409 responses and optionally also geo-location from all personnel and provides reports to all subscribed parties, indicating exceptions where further action is needed. In one embodiment, the personnel tracking subsystem 205 logs the responses in the system database 201 and makes them available for future data and trend analysis.

Figure 6:
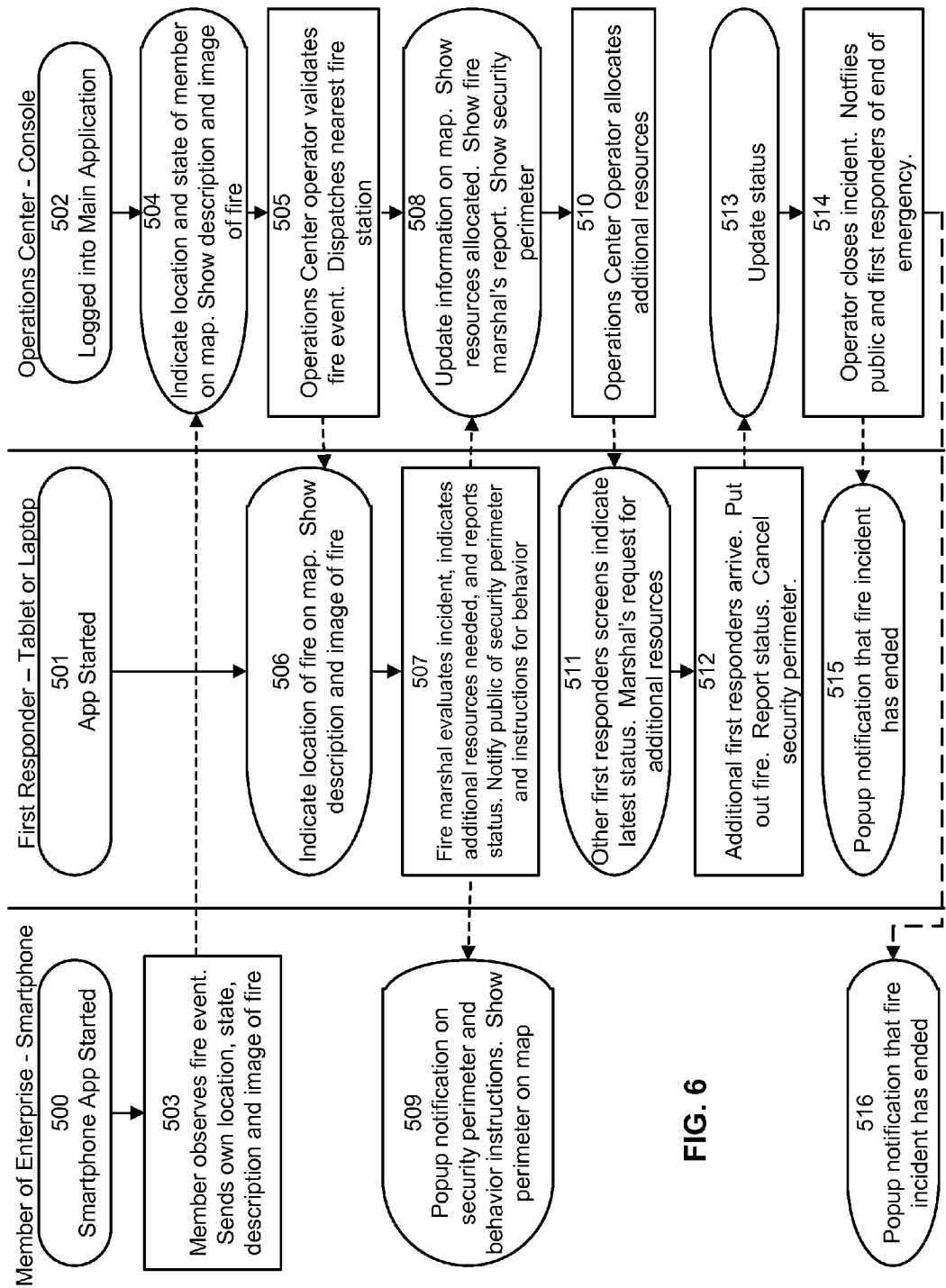
FIG. 6 is a diagram illustrating the proliferation of situational awareness between computing devices of different constituents, according to one embodiment.

FIG. 6 illustrates the proliferation of situational awareness between computing devices of different constituents, according to one example embodiment. The diagram emphasizes the visual and textual information available to the various enterprise constituents, using a fire event use-case as an example. The diagram depicts the views presented to users in three different constituent roles within the enterprise: an operations center operator, a fire marshal, and a member of the enterprise. The view on a particular device is dependent upon the corresponding individual's role in relation to the enterprise. Although there are three roles shown in the diagram, any number of roles, and consequently any number of views, can be supported.

After the three devices are started and their respective users logged in (500, 501 and 502), a member of the enterprise observes a fire and, using her smartphone 110 running the invention's mobile app 207, composes and sends a report 503 describing the observed event, her own status (e.g., "safe" or "in danger"), and an image or video she has taken of the fire. Before sending the report, the app 207 automatically adds the mobile device's location and time-stamps the report. The report is then sent into the appropriate system 200 through the enterprise's Personal Safety Service 206 (assuming one is used by the enterprise).

The report is received by the system 200 and automatically, semi-automatically, or manually classified and processed by the application 200, specifically, by the application's Inbound Event Manager 600. The operator role's view, which subscribes, amongst other types of events, to fire events, flashes an alert on the operator's view, indicating the fire event, the event location, and the state of the member who sent the report on a map display. Upon the operator's request, the full description (e.g., the text, image and/or video) of the fire event is displayed 504 on his view. The operator validates the event as per the enterprise's standard operating procedures and dispatches the appropriate firefighting team 505.

The fire marshal's view also subscribes to fire events. Upon receiving of the fire event, the fire marshal's display indicates the location of the fire on the map 506. The fire marshal queries the system and his view expands to include all available information related to the event. Once the fire marshal evaluates the incident, he decides that additional resources are needed, that a security perimeter around the location is to be established, and that members of the enterprise and the public should stay behind the perimeter. Using his own device 110, the fire marshal sends the appropriate messages to the system 507 to establish the perimeter and indicate the corresponding instructions that should be issued. In one embodiment, the perimeter is a pre-determined shape (e.g., circular) with the fire marshal setting the radius. In another embodiment, the fire marshal defines the perimeter by drawing it on the map (e.g., by drawing with a stylus on a touchscreen). In other embodiments, hybrid methods are used, such as initially defining the perimeter to be circular, but enabling the fire marshal to move the edges to account for specific features, such as extending the perimeter to take advantage of a natural bottleneck at one end that is easier to close off.

The Operations Center operator's view is updated with the information originated by the fire marshal, indicating the resources already allocated and additional resources requested. The Operation Center operator's map is updated to show the security perimeter 508. All members of the enterprise receive a notification showing the security perimeter on their mobile devices' maps along with the corresponding instructions to stay behind the security perimeter 509. In cases other than fire (e.g., a report of an unknown biological agent), personnel inside the security perimeter may be instructed to stay within the perimeter in order to prevent the spread of the unknown biological agent.

The Operation Center operator and fire dispatcher allocate additional first responder resources. The allocated resources are displayed on the Operation Center and the fire marshal's views 510. All additional first responders' views are updated to reflect the most current status of the event 511. The first responder resources collaborate in putting out the fire and other rescue operations and report the status into the system 512, which is updated on all subscribed views 513.

The Operations Center operator closes the incident. Using the system, he notifies the members of the enterprise, the general public, and the first responders as to the end of the emergency 514. These notifications pop up on the first responders' 515 and the members' 516 views. In a similar manner, the geographical markings showing the security perimeter that was established by the fire marshal are removed from all views.

Figure 7:
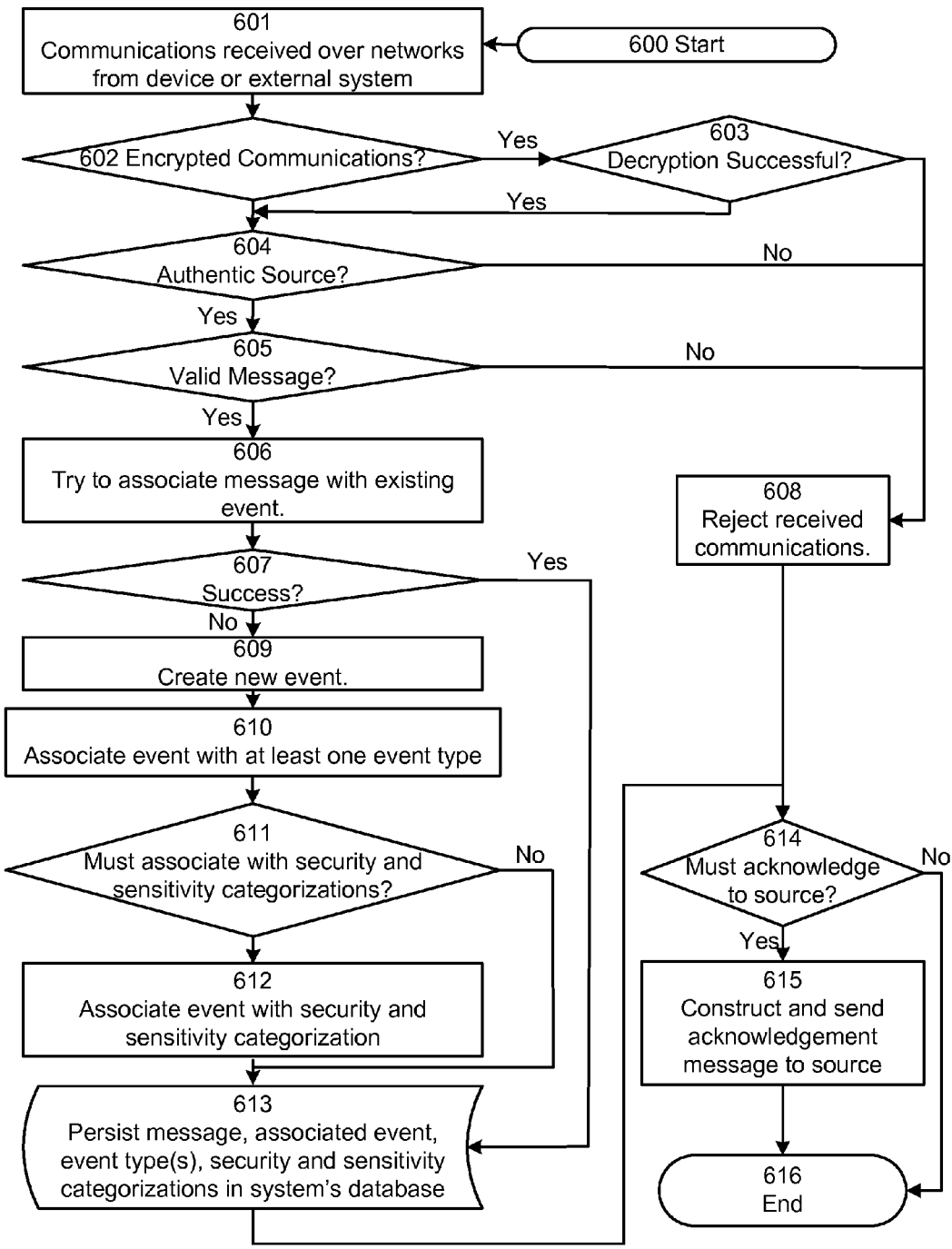
FIG. 7 is a flow-chart illustrating a method for processing a message received by a crisis communications management system, according to one embodiment.

FIG. 7 illustrates an example method for a crisis communications management system (such as the one illustrated in FIG. 1) to process a received message, according to one embodiment. FIG. 7 attributes the steps of the method to the inbound event manager (IEM) subsystem 202, but in other embodiments, some or all of the steps are performed by other entities in the system. In addition, some of the steps may be performed in a different order and/or in parallel. The IEM subsystem 202 manages the flow and processing of event reports arriving into the system from multiple sources (e.g., personnel, other organizations, individuals, and other systems); such events may include emergency situations reported by individuals, field reports from first responders, events coming from physical security sensors such as video surveillance systems, and the like. In one embodiment, an event report includes some or all of: a textual description of the situation, the source of the event report, multimedia content related to the event, and the event's geo-location. The IEM subsystem 202 applies business logic to the incoming influx of events, allowing effective processing during emergency situations, e.g., by routing events to the appropriate system constituents along with shared situational maps and notifying the appropriate teams.

After the IEM process is started 600, the IEM subsystem 202 waits for communications to be received 601 over the network from any device or external system. As applicable, encrypted communications are decrypted 603, authenticated 604, and the message contained in the communications is validated 605. Any communication that is not decrypted, authenticated or validated successfully is rejected 608 and is not processed further.

If a message is successfully authenticated 604 and validated 605 (and decrypted 603 if necessary) then the IEM subsystem 202 attempts to associate 606 the message with an existing event. If successful 607, the message is persisted 613 as part of the associated event 613. If no event can be associated with the message, the IEM subsystem 202 creates 609 a new event, associates 610 the event with at least one event type, and, if system settings require 611 classification by security and/or sensitivity categories, it does so 612. The IEM subsystem 202 persists 613 the message as part of the newly created associated event.

If the originator of the communication requires 614 acknowledgment that the communication was successfully received and processed, the IEM subsystem 202 constructs and sends 615 an acknowledgment message to the originating device or system. The process then idles and waits 616 for the next communication message.

Figure 8:
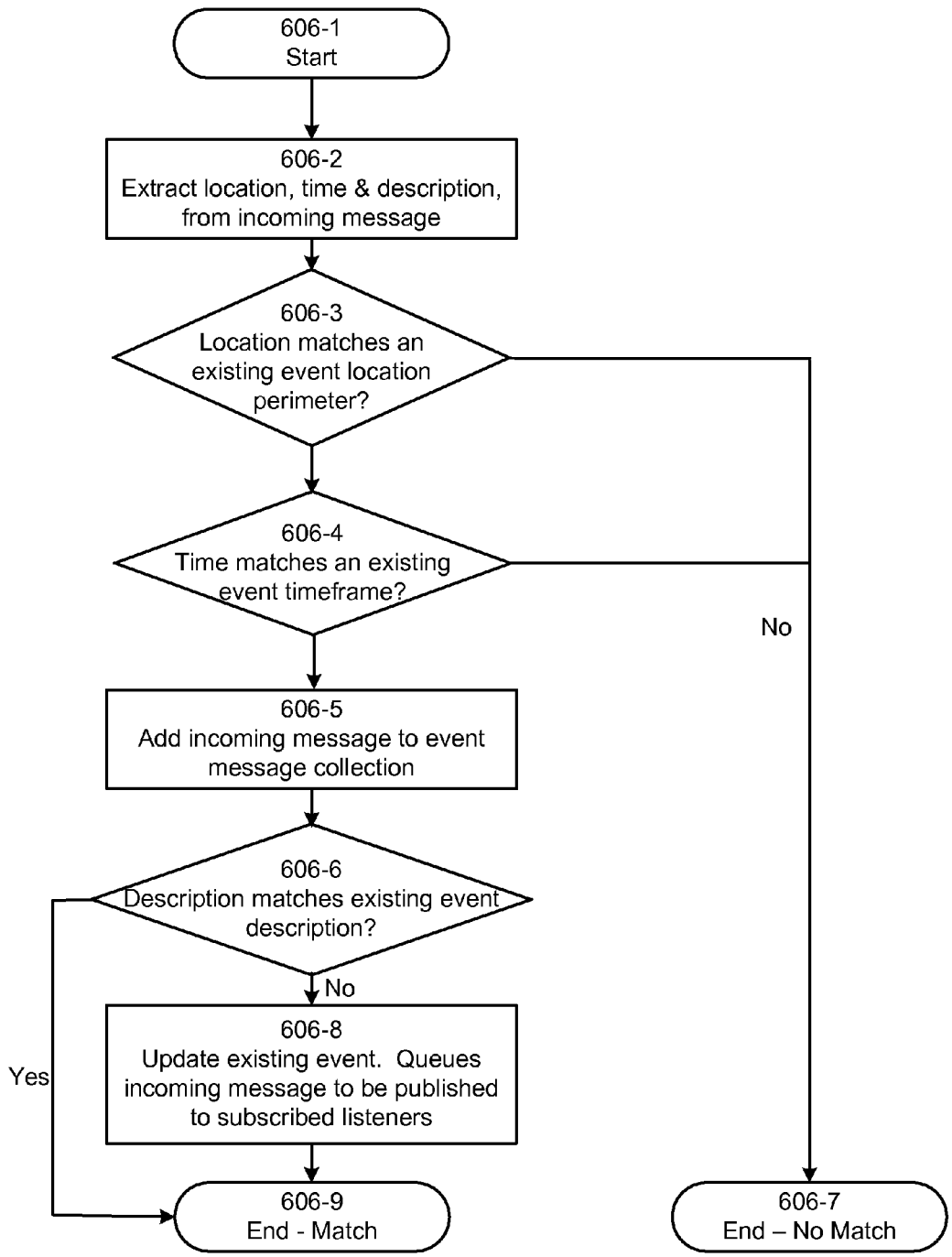
FIG. 8 is a flow-chart illustrating a method for associating a message with an existing event, according to one embodiment.

FIG. 8 illustrates a method for a crisis communications management system (such as the one illustrated in FIG. 1) to associate 606 a message with an existing event, according to one embodiment. FIG. 8 attributes the steps of the method to the IEM subsystem 202, but in other embodiments, some or all of the steps are performed by other entities in the system. In addition, some of the steps may be performed in a different order and/or in parallel.

During crisis events, operations centers are typically flooded with messages from personnel and automated systems describing what may essentially be the same incident. Associating messages that refer to a single real-world crisis event with a single event within the system can therefore massively improve efficiency in the management of emergency incidents. In this way, decision makers in charge of managing the incident can be presented with a more coherent picture and not be overwhelmed with redundant and/or duplicative data.

After the process starts 606-1, the IEM subsystem 202 extracts 606-2 metadata (e.g., location, time and description information) from the incoming message. The IEM subsystem 202 determines whether the metadata extracted from the message matches information describing an existing event, within a threshold tolerance. In one embodiment, if the extracted location matches 606-3 the location of an existing event within a specified distance and the message time matches 606-4 the time of an existing event within a specified time span the system adds the incoming message to the collection of messages associated with the existing event. Otherwise, the IEM subsystem 202 determines 606-7 that no match was found and proceeds to create 609 a new event.

If the association was successful the IEM subsystem 202 uses an algorithm to attempt to match 606-6 the description contained in the incoming messages with the description contained in the matched event. In one embodiment, the IEM subsystem 202 matches 606-6 incoming descriptions contained in messages with the description of the event based on shared common key words (e.g., "fire," "flood," etc.). In other embodiments, the IEM subsystem 202 uses other criteria to match incoming descriptions in messages with events, such as automated comparison of multi-media data included in the messages and information associated with the event. For example, if an event is of the "fire" type and the incoming message includes an image of a fire, a match may be determined. Conversely, if the image shows a car crash, the IEM subsystem 202 may create a new event instead.

If the IEM subsystem 202 determines that there is substantially new information in the incoming message, it updates 606-8 the description of the existing event and queues the incoming message to be published to authorized interested parties that subscribe to this type of information. In one embodiment, an operator may at any point view the information, and decide to merge an incoming message to an existing event, or de-couple a message from an associated event to create a new event, if needed.

Figure 9:
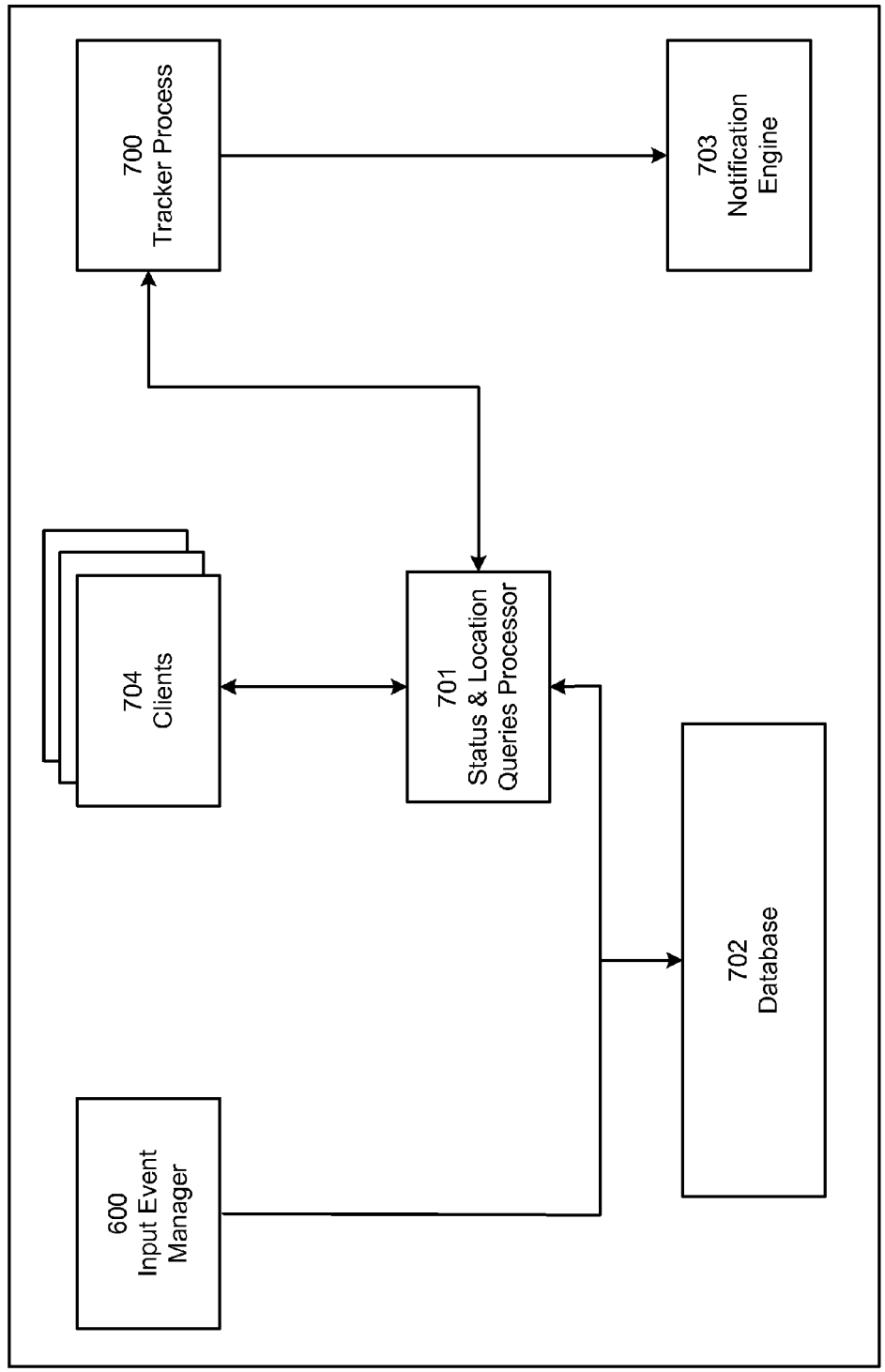
FIG. 9 is a high-level diagram illustrating a sub-system for providing personnel status tracking, according to one embodiment.

FIG. 9 illustrates one embodiment of a personnel status tracking (PST) subsystem 205 that offers real-time visibility and detailed information regarding enterprise members' location, condition, and status. The Operations Center uses the PST subsystem 205 to solicit accountability status from select groups or the entire enterprise population and collect accurate accountability (e.g., status, condition, and location) reports. In one embodiment, individuals may also provide unsolicited reports of their current status and location.

In one embodiment, the PST subsystem 205 operates using the "management by exception" concept, namely managing those individuals that either do not report when expected (e.g., their statuses are "unknown" or "stale") or report an abnormal condition. The PST subsystem 205 provides awareness of personnel location, circumstances, and needs across multiple teams. The PST subsystem 205 may also provide real-time reporting. Thus, the operator can be provided with a single aggregated dashboard that "drills down" to granular organizational detail.

In one embodiment, the PST subsystem 205 provides personnel status and accountability functionality, including: capturing status from individuals, maintaining history of personnel status, proactively soliciting individuals to report their status, targeting specific groups for follow-up reporting based on their status, viewing real-time personnel accountability reports, enabling entry of personnel status by proxy (e.g., by a system operator), enabling "check-in" reporting of user status (e.g., "I am here and OK"), and enabling "check-out" reporting of user status (e.g., "do not worry about me").

In the embodiment shown in FIG. 9, the PST subsystem 205 is based around a tracker process 700. This free-running process 700 is responsible for managing the operation of the PST subsystem 205. The PST subsystem 205 keeps track of the messages from members of the enterprise logged at the Database 702, which automatically notifies the Tracker Process 700 every time the system receives a message from a member of the enterprise, either via the Input Event Manager 600 or inputted manually by proxy at one of the clients 704. The messages can include, but are not limited to, event reports, responses to requests to report status, and/or events automatically generated by the event triggers system 103-4, such as access control events generated automatically when scanning personnel badges (e.g., "person X just entered location Y at time Z").

In one embodiment, the Tracker Process 700 keeps track of all status and location messages from members of the enterprise, whether the reports are solicited or unsolicited, sends requests to selected members of the enterprise for their status and location, via the Notification Engine 703, tracks unanswered solicitation to members of the enterprise for their status and location, aggregates and correlates the status and location of members into various reports which can be displayed automatically on any one of the authorized clients 704 by triggering an update through the Status and Location Queries Processor 701.

Figure 10:
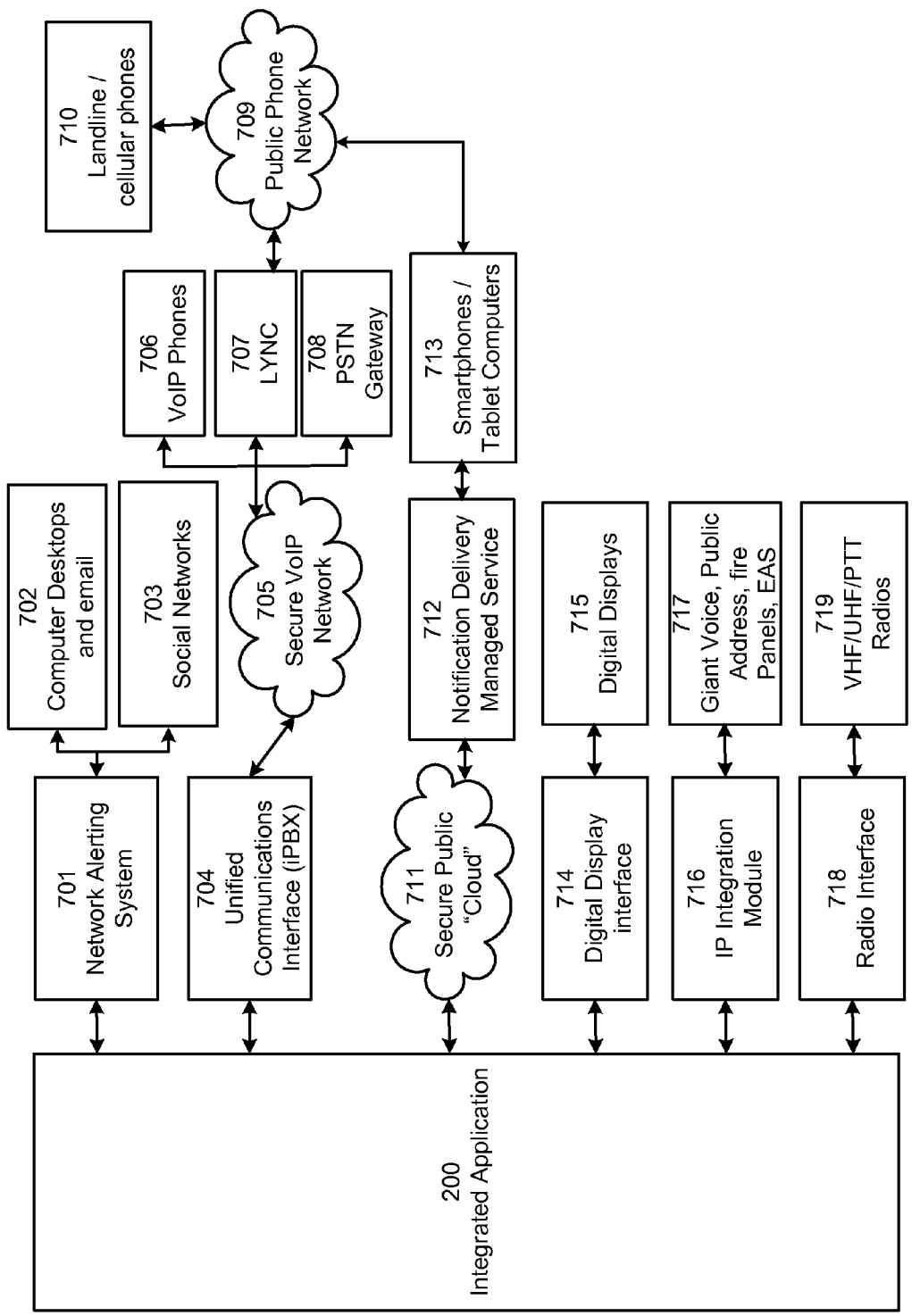
FIG. 10 is a high-level diagram illustrating a unified emergency notification system, according to one embodiment.

FIG. 10 illustrates an embodiment of an integrated emergency notification system, including an integrated application 200. The integrated application 200 unifies and automates the end-to-end emergency notification process across the entire enterprise. Using a web-based console, smartphone or tablet devices, operators can activate alerts and receive responses from any location to virtually any notification device or system.

The NAS 701 delivers audio/visual pop-up notifications to computer desktops and email systems 702 as well as the constituents' responses from those devices. It also sends notifications to constituents via the social networks 703 (e.g., FACEBOOK and TWITTER) that the constituents subscribe to. Email is delivered and received using secure methods, such as digital signing using public-key infrastructure (PKI).

The Unified Communications Interface (iPBX) 704 delivers and receives text, image and video messages through the enterprise's secure Voice over IP (VoIP) Network 705 to the enterprise's VoIP Phones 706 and/or MICROSOFT's LYNC unified communications platform 707. It also delivers voice alerts to landline and cellular phones 710 via a Public Switched Telephone Network (PSTN) Gateway 708 and the public phone network (709) as well as to on-site or hosted mass dialing services.

The Notification Delivery Managed Service (NDMS) 712, which is interfaced to the system via a secure public cloud 712, delivers and receives text, image and image alerts to smart phones and tablet devices. Supported smart phones and tablet devices may also provide location information to the system via the NMDS 712.

The Digital Display Interface 714 delivers text, video and video alerts to supported digital display systems 715.

The IP Integration Module 716 interfaces to a variety of non-IP notification systems 715, such as Giant Voice, sirens, public address, voice-capable fire alarm control panels, in-building fire notification panels and local radio and television stations via the Emergency Alerting System (EAS).

The Radio Interface 718 delivers voice messages to a variety of first-responder and security forces Land Mobile Radio (LMR) systems 719, including VHF, UHF and Press-to-Talk (PTT) radios. Supported radios may also provide the system with location information through their built-in GPS.

Exemplary Use Case

The following exemplary use case explains how the components identified above can interact to provide crisis notification management and shared situational awareness in an embodiment configured for use by law enforcement. A law enforcement official observes a vehicle leaving the scene of a crime and creates an event report identifying it as a vehicle of interest using a mobile application 207 running on the law enforcement official's mobile device 110. The mobile application sends a message to the integrated application 200 including the event report. In one embodiment, the event report includes an identification of the law enforcement official, the location of the event, the time of the event, and information about the vehicle (e.g., a white Chevy Impala with the license plate 'SUSPECT' heading North). The event report can also include pictures, video, audio, textual commentary, and other types of multi-media data, as available. For example, the message can include dash-board camera footage from the law enforcement official's car from around the time of the reported event, automatically attached by the mobile application 207, as well as a photograph of the vehicle of interest taken and manually added to the report by the law enforcement official.

Depending on the embodiment, the identification of the law enforcement official included in the event report includes the serial number of the mobile device 110, a username, the official's badge number, the official's name and rank, and/or any other available information that can be used to identify the official from which the report originates.

Depending on the embodiment, the location and time of the event is determined automatically by the mobile application 207 (e.g., using GPS and internal clock functions of the mobile device 110) and/or manually, via user input from the law enforcement official. In one embodiment, the location and time are automatically determined unless the law enforcement official provides this information, thereby overriding the automatic determination. For example, if the law enforcement official observes the event while in a dangerous situation and retreats to a safe location before reporting the event, the law enforcement official can provide the location and time of the actual event, rather than using the automatically determined current time and location.

In one embodiment, the message including the event report is sent to the integrated application 200 via a PSS 206, which screens the message for harmful content before forwarding it on to the integrated application. In other embodiments, the PSS 206 or other routing mechanism delivers the message from the mobile device 110 to the integrated application 200.

Once the message is received by the integrated application 200, it is processed by the inbound event management system 202, which inspects the message and, in this case, determines that it includes a report of a vehicle of interest. In one embodiment, the inbound event management system 202 queries the system database 201 using the identification information provided in the report to validate that report originates from a registered law enforcement official.

Once the report has been validated (if required), the unified crisis notification subsystem 204 queries the system database to identify all law enforcement officials and/or stations that are currently monitoring or available to monitor roads in the vicinity of the event (as determined by the personnel tracking subsystem 205). The unified crisis notification subsystem 204 then sends a message to some or all of the identified law enforcement officials and/or stations identifying the vehicle of interest and requesting confirmation of receipt. In one embodiment, the message is sent to the mobile devices 110 and 112 of all identified law enforcement officials as well as computer systems housed within law enforcement stations (e.g., police barracks). In others embodiment, the message is sent only to those devices 103, 110 and 112 that are deemed to be secure, such as those connected to private networks within stations. While this somewhat reduces the availability of information to law enforcement officials in the field in the short term, it also prevents the information included therein becoming public, which may tip off the suspect and reduce the chances of capture. In one such embodiment, the unified crisis notification subsystem 204 attempts to send messages to all of the identified recipients and the messages are filtered by the PSS 206 to ensure network security is maintained and sensitive information is not transmitted over unsecure public networks (e.g., a wireless carrier network 109).

The messages distributed by the unified crisis notification subsystem 204 distribute the information included in the initial report provided by the law enforcement official that witnessed the event. The receiving computing devices (e.g., station computers 103, officials' mobile devices 110 and 112, etc.) present the information (or a subset thereof) from the report to other law enforcement officials. In some embodiments, the messages also include a request to verify successful distribution of the information. In one such embodiment, confirmation is sent to the integrated application automatically on display of the information. In another such embodiment, the user is prompted to confirm receipt (e.g., by making a specified user input), with confirmation being sent to the integrated application 200 when receipt is confirmed. In this way, an operator of the integrated application 200 (e.g., at a command & control center) knows not just that the message was sent out, but that the content of the message was viewed. The responses can also include location information that is used by the personnel tracking subsystem 205 to update the location of personnel in the field. This location information can be in the form of generated location data (e.g., a current GPS location, cell-tower location data, etc.) or based on information provided by the personnel (e.g., "I am currently at the intersection of 25$^{th}$ and 4$^{th}$).

The shared situational awareness subsystem 203 provides an overview of the event and the distribution of information regarding the event. The integrated application 200 provides a map of the area surrounding the event that is overlaid with available information relating to the event. The operator can be provided with interactive controls for manipulating the map display, such as zooming in and out, scrolling the map, filtering the information that is overlaid, and the like. In one embodiment, the map is overlaid with an indication of the location included in the initial report, the locations of all law enforcement officials in the area (as determined by the personnel tracking subsystem 205), and the location of additional reports submitted that relate to the event. The operator can drill down and view additional information included in reports and/or about personnel by selecting the corresponding indicators on the map. The overlaid information also indicates which law enforcement officials have received the information regarding the vehicle of interest.

The shared situational awareness subsystem 203 can also display additional information received by the inbound event management subsystem 202 from the mobile devices 110 of personnel in the field. For example, if law enforcement officials see what they believe to be the vehicle of interest, they may report it using the mobile application 207. These reports are processed by the integrated application 200, and if verified, added to the map provided the shared situational awareness subsystem 203. In this way, the operator can analyze potential sightings of the vehicle of interest to determine whether they are likely to be genuine sightings or false positives. In one embodiment, this additional information is automatically pushed to the devices of personnel in the field (if the security requirements required by the PSS 206 allow). In another embodiment, such additional information is only distributed if the operator determines that it is relevant and/or correct.

The map and overlaid information (as well as additional information available by drilling down in particular reports/personnel representations) allows the operator to quickly evaluate the overall situation relating to the vehicle of interest. In this way, the operator can easily determine where gaps in coverage exist through which the vehicle of interest could escape and either request additional law enforcement officials who are already aware of the event move to new locations, or distribute the report to additional personnel in order to increase coverage.

In some embodiments, the shared situational awareness subsystem 203 makes the map and overlaid information available in the command & control center (or a subset thereof) to the mobile devices 110 of personnel in the field. In this way, all of the law enforcement officials involved in the search for the vehicle of interest can quickly make informed decisions regarding what actions to take at any given time. For example, a group of official's at a station may elect to split up to fill a nearby gap in coverage, without requiring direct instruction from the command & control center. In one embodiment, personnel in the field can report such intended actions to the integrated application 200, via the mobile application 207. In this way, the operator at the command & control center can see not just the current situation, but also how the situation is evolving, and issue new instructions where necessary. For example, if two groups of personnel in the field decide to move to fill the same gap in coverage, the operator can intervene and direct one to take an alternative course of action.

The unified crisis notification subsystem 204 also enables law enforcement to distribute information to the public. For example, if the operator in the command & control center determines, based on the map and overlaid data provided by the shared situational awareness subsystem 203, that the vehicle of interest is heading East and driving in a manner that puts the public in danger, the operator can distribute a message to the public warning them of the potential danger. This message can be delivered via one or more channels, including messages to mobile devices 110, public announcement systems 115, social networks 115, and the like. Thus, law enforcement can effectively control what information is kept secure and what information is made publicly available, based on operational and public safety factors on a case-by-case basis as the event develops.

Once the event has reached a resolution (e.g, the vehicle of interest has been stopped by a law enforcement official and the driver detained), the operator in the command & control center records the event resolution in the integrated application 200. The unified crisis notification subsystem 204 distributes notifications that the event has been resolved to personnel and other interested individuals in the field, as appropriate in view of the role-based security and access permission protocols in place. In addition, the shared situational awareness subsystem 203 updates the map display provided at the command & control center and by the mobile applications 207 of personnel. In one embodiment, the shared situational awareness subsystem 207 removes all indications of the event from the map immediately upon resolution. In another embodiment, the event remains on the map for a period of time (e.g., a for a fixed time, until removed by an operator, etc.) but is visually distinguished as resolved (e.g., by being presented in a different color to unresolved events).

Computing Machine Architecture

Figure 11:
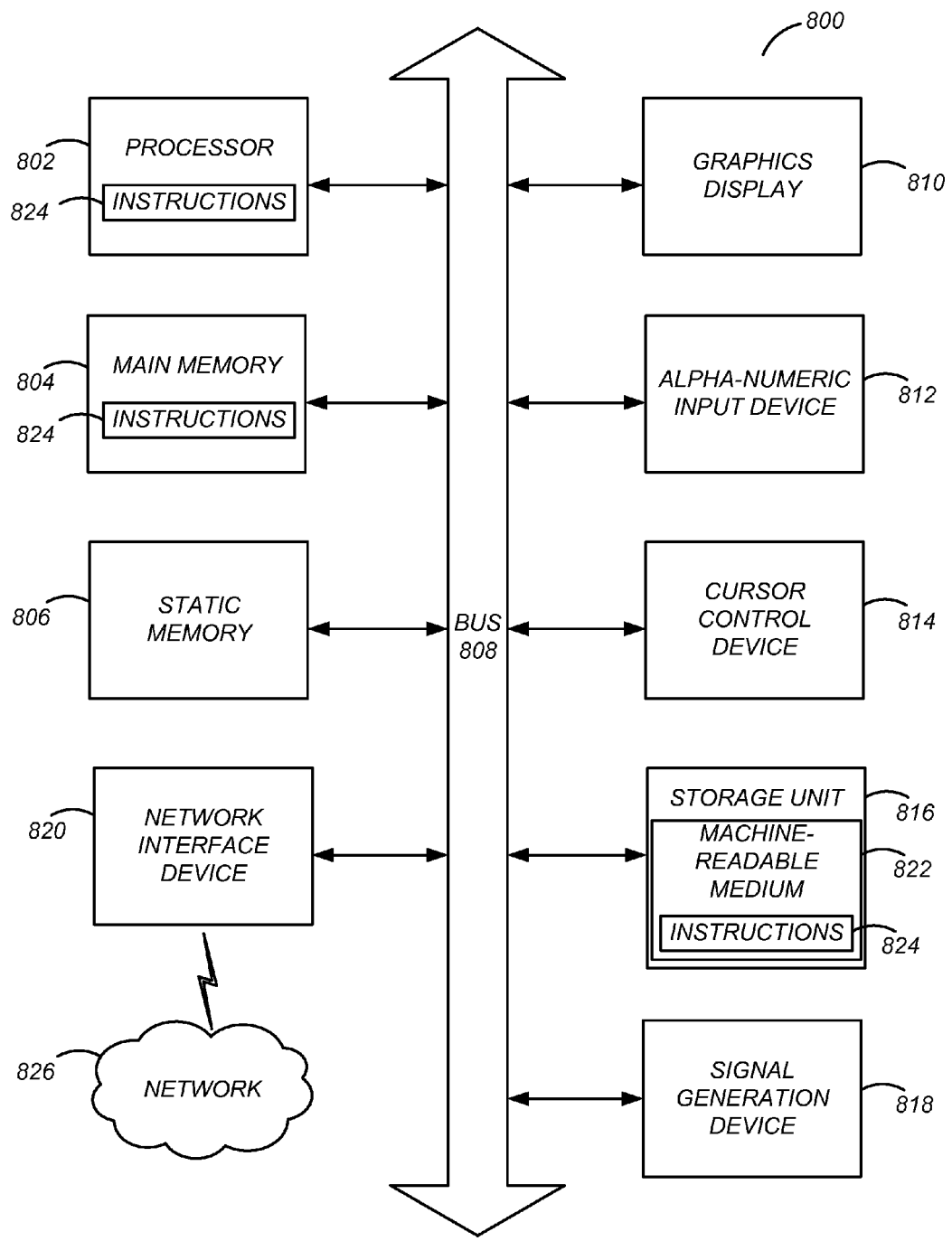
FIG. 11 illustrates one embodiment of components of an example machine able to read instructions from a machine-readable medium and execute them in a processor (or controller).

The disclosed software structures and processes are configured for operation on a machine, e.g., a computing system. FIG. 11 is a block diagram illustrating components of an example machine able to read instructions from, for example, a non-transitory machine-readable medium and execute them in one or more processors (or controllers). In some embodiments, specialized machines configured to perform some or all of the functionality described herein are used. Specifically, FIG. 11 shows a diagrammatic representation of a machine in the example form of a computer system 800 within which instructions 824 (e.g., software or program code) for causing the machine to perform any one or more of the methodologies discussed herein may be executed. The methodologies include those described with FIGS. 5-8. In alternative embodiments, the machine operates as a standalone device or may be connected (e.g., networked) to other machines. In a networked deployment, the machine may operate in the capacity of a server machine or a client machine in a server-client network environment, or as a peer machine in a peer-to-peer (or distributed) network environment.

The machine 800 for this configuration may be a mobile computing devices such as a tablet computer, an ultrabook (or netbook) computer, a personal digital assistant (PDA), a cellular telephone, a smartphone, a web appliance, or like machine capable of executing instructions 824 (sequential or otherwise) that specify actions to be taken by that machine. Further, while only a single machine is illustrated, the term "machine" shall also be taken to include any collection of machines that individually or jointly execute instructions 824 to perform any one or more of the methodologies discussed herein.

The example computer system 800 includes one or more processors 802 (e.g., a central processing unit (CPU) and may also include a graphics processing unit (GPU), a digital signal processor (DSP), one or more application specific integrated circuits (ASICs), one or more radio-frequency integrated circuits (or chipset) (RFICs), a wireless fidelity (WiFi) chipset, a global positioning system (GPS) chipset, an accelerometer (one, two, or three-dimensional), or any combination of these). The computer system 800 also includes a main memory 804 and a static memory 806. The components of the computing system 800 are configured to communicate with each other via a bus 808. The computer system 800 may further include graphics display unit 810 (e.g., a plasma display panel (PDP), a liquid crystal display (LCD), glass display) which may be configured for capacitive or inductive touch sensitivity to allow for direct interaction with software user interfaces through the display 810. The computer system 800 may also include alphanumeric input device 812 (e.g., a keyboard), a cursor control device 814 (e.g., a mouse, a trackball, a joystick, a motion sensor, or other pointing instrument), a storage unit 816, a signal generation device 818 (e.g., a speaker), and a network interface device 820, which also are configured to communicate via the bus 808.

The storage unit 816 includes a machine-readable medium 822 on which is stored instructions 824 (e.g., software) embodying any one or more of the methodologies or functions described herein. The instructions 824 (e.g., software) may also reside, completely or at least partially, within the main memory 804 or within the processor 802 (e.g., within a processor's cache memory) during execution thereof by the computer system 800, the main memory 804 and the processor 802 also constituting machine-readable media. The instructions 824 (e.g., software) may be transmitted or received over a network 826 via the network interface device 820.

While machine-readable medium 822 is shown in an example embodiment to be a single medium, the term "machine-readable medium" should be taken to include a single medium or multiple media (e.g., a centralized or distributed database, or associated caches and servers) able to store instructions (e.g., instructions 824). The term "machine-readable medium" shall also be taken to include any medium that is capable of storing instructions (e.g., instructions 824) for execution by the machine and that cause the machine to perform any one or more of the methodologies disclosed herein. The term "machine-readable medium" includes, but not be limited to, data repositories in the form of solid-state memories, optical media, and magnetic media.

Additional Configuration Considerations

Throughout this specification, plural instances may implement components, operations, or structures described as a single instance. Although individual operations of one or more methods are illustrated and described as separate operations, one or more of the individual operations may be performed concurrently, and nothing requires that the operations be performed in the order illustrated. Structures and functionality presented as separate components in example configurations may be implemented as a combined structure or component. Similarly, structures and functionality presented as a single component may be implemented as separate components. These and other variations, modifications, additions, and improvements fall within the scope of the subject matter herein.

Various implementations of the systems and techniques described here can be realized in digital electronic and/or optical circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications, scripts, or program code) include machine instructions, e.g., 824, for a programmable processor, e.g., 802, and can be implemented in a high-level procedural and/or object-oriented programming language, and/or in assembly/machine language. The computer programs can be structured functionality in units referenced as "modules," for example, as illustrated in FIG. 10. As used herein, the terms "machine-readable medium" and "computer-readable medium" refer to any computer program product, non-transitory computer readable medium, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term "machine-readable signal" refers to any signal used to provide machine instructions and/or data to a programmable processor.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

While this specification contains many specifics, these should not be construed as limitations on the scope of the disclosure or of what may be claimed, but rather as descriptions of features specific to particular implementations of the disclosure. Certain features that are described in this specification in the context of separate implementations can also be implemented in combination in a single implementation. Conversely, various features that are described in the context of a single implementation can also be implemented in multiple implementations separately or in any suitable sub-combination. Moreover, although features may be described above as acting in certain combinations and even initially claimed as such, one or more features from a claimed combination can in some cases be excised from the combination, and the claimed combination may be directed to a sub-combination or variation of a sub-combination.

Similarly, while operations are depicted in the drawings in a particular order, this should not be understood as requiring that such operations be performed in the particular order shown or in sequential order, or that all illustrated operations be performed, to achieve desirable results. In certain circumstances, multi-tasking and parallel processing may be advantageous. Moreover, the separation of various system components in the embodiments described above should not be understood as requiring such separation in all embodiments, and it should be understood that the described program components and systems can generally be integrated together in a single software product or packaged into multiple software products.

A number of implementations have been described. Nevertheless, it will be understood that various modifications may be made without departing from the spirit and scope of the disclosure. Accordingly, other implementations are within the scope of the following claims. For example, the actions recited in the claims can be performed in a different order and still achieve desirable results.

Upon reading this disclosure, those of skill in the art will appreciate still additional alternative structural and functional designs for a personnel communications management system through the disclosed principles herein. Thus, while particular embodiments and applications have been illustrated and described, it is to be understood that the disclosed embodiments are not limited to the precise construction and components disclosed herein. Various modifications, changes and variations, which will be apparent to those skilled in the art, may be made in the arrangement, operation and details of the method and apparatus disclosed herein without departing from the spirit and scope defined in the appended claims.

What is claimed is:

1. An integrated personnel crisis communications management system for distributing information to users associated with an enterprise, comprising:
   a computer database including data about a plurality of users and an event record storing information about an event related to the enterprise;
   an inbound event management subsystem operably connected to the database, the inbound event management subsystem, responsive to receiving a new communication, classifies the new communication as corresponding to the event and supplements the information about the event based on the new communication;
   a notification subsystem operably connected to the inbound event management subsystem, the notification subsystem sending, responsive to the new communication, a notification to one or more devices associated with users;
   a shared situational awareness subsystem operably connected to the database, the shared situational awareness subsystem providing to a first user device associated with a first user of the plurality of users, responsive to the new communication, a first subset of the information about the event for presentation in a user interface, and providing to a second user device associated with a second user of the plurality of users, responsive to the new communication, a second subset of the information about the event for presentation in a user interface, the first subset being determined based on data about the first user stored in the database and the second subset being determined based on data about the second user stored in the database; and
   a personnel tracking subsystem tracking the status of a plurality of tracked users, the tracking comprising:
      receiving status updates from a first subset of a plurality of user devices, each user device associated with a corresponding tracked user, and each response including a status for the corresponding tracked user;
      identifying a second subset of the user devices from which recent status updates have not been received;
      determining, for each of the second subset of the user devices, an inferred status for the corresponding tracked user, the inferred status based on previous status information associated with the corresponding tracked user; and
      aggregating the statuses and inferred statuses of the tracked users for presentation.

2. The integrated personnel crisis communications management system of claim 1, wherein classifying the new communication as corresponding to the event comprises:
   comparing metadata included in the new communication with data describing the event in the event record; and
   determining the new communication corresponds to the event if the metadata included in the new communication matches the data describing the event, within a threshold tolerance.

3. The integrated personnel crisis communications management system of claim 1, wherein the inbound event management subsystem adds an additional event record to the database responsive to receiving an additional communication not related to the event, and adds information to the additional event record based on the additional communication.

4. The integrated personnel crisis communications management system of claim 1, wherein the notification subsystem sends an additional notification to a notification device associated with the enterprise responsive to the new communication.

5. The integrated personnel crisis communications management system of claim 4, wherein the device is one of: a networked computer; a smart-phone; an IP phone; a tablet; a satellite phone; a landline phone; a mobile phone; a social network server configured to distribute the additional notification through via a social network; a speaker system; a display board; a TV system; a Land Mobile Radio; a Voice-Enabled Fire Alarm Control Panel; and a web site server configured to add the additional notification to a web site feed.

6. The integrated personnel crisis communications management system of claim 1, wherein the new communication is received from a device and the inbound event management subsystem, on receiving the new communication, performs processes including:
   authenticating credentials of the device;
   validating content contained within the communication; and
   acknowledging receipt of the new communication to the device.

7. The integrated personnel crisis communications management system of claim 1, wherein the new communication is received from an automated system associated with the enterprise and the inbound event management subsystem, responsive to receiving the new communication, performs processes including:
   authenticating credentials of the automated system; and
   validating content contained within the communication.

8. The integrated personnel crisis communications management system of claim 1, wherein the inbound event management subsystem associates the event with a security/sensitivity categorization based on the communication and stores the security/sensitivity categorization in the event record, the one or more devices to which the notification is sent being determined based on the security/sensitivity categorization.

9. The integrated personnel crisis communications management system of claim 1, wherein the communication includes at least one of the following types of information: location, image, audio, and video.

10. The integrated personnel crisis communications management system of claim 1, wherein the first subset of the information about the event is determined based on at least one of: a type of the event; a role of the first user in relation to the enterprise; a role of the first user in relation to the type; a geographical location of the first user; a geographical location associated with the communication; characteristics of a device being used by the first user to view first subset; and characteristics of a network connecting the management system to the device.

11. The integrated personnel crisis communications management system of claim 1, wherein the statuses and inferred statuses are presented by:
providing a dashboard display indicating the status of viewed users, the viewed users being a subset of the tracked users;
providing user interface controls in conjunction with the dashboard display for at least one of: viewing the status of a selected one of the viewed users in greater detail, filtering the viewed users based on status, filtering the viewed user based on location, filtering the viewed users based on assigned roles, and filtering the viewed users based on recency of status updates.

12. A computer-implemented method for personnel crisis communications management for an enterprise, comprising:
receiving, a first message including new information about an event;
analyzing the first message to determine a correspondence between the event and an event entry in a database, the database including a plurality of event entries, each containing existing information about a corresponding event;
adding the new information to the event entry in the database responsive to the determined correspondence;
comparing the new information to existing information about the corresponding event in the database, the comparing comprising:
identifying keywords in the new information;
identifying keywords in the existing information; and
determining the new information to be substantially different to the existing information responsive to the new information including a keyword not present in the existing information;
identifying a first subset of users and a second subset of users based on information about users stored in a database;
generating, responsive to the new information being substantially different to the existing information, a first report about the event based on: the new information, the event entry, and information stored in a database about the first subset of users;
generating, responsive to the new information being substantially different to the existing information, a second report about the event based on: the new information, the event entry, and information stored in a database about the second subset of users;
transmitting the first report to user devices associated with the first subset of users; and
transmitting the second report to user devices associated with the second subset of users.

13. The method of claim 12, wherein the analyzing comprises:
comparing location data included in the first message with location data included in the event entry;
comparing time data included in the first message with time data included in the event entry; and
determining that the event corresponds to the event entry responsive to the comparing location data and the comparing time data.

14. The method of claim 12, wherein analyzing the first message comprises:
comparing position information included in the first message with position information associated with the event entry to determine a position similarity;
comparing time information included in the first message with time information associated with the event entry to determine a time similarity; and
determining the correspondence between the event and the event entry responsive to the position similarity being greater than a position threshold and the time similarity being greater than a time threshold.

15. The method of claim 12, further comprising:
receiving position data for a plurality of enterprise personnel at regular time intervals, the position data indicating a location of corresponding enterprise personnel when the data was sent; and
displaying, to a user, the location of at least one of the plurality of enterprise personnel.

16. The method of claim 12, further comprising:
requesting status updates from a plurality of enterprise personnel;
receiving a status update from at least one of the plurality of enterprise personnel, the status update including a current status; and
displaying the current status to a user.

17. The method of claim 12, further comprising:
adding additional information to the event entry responsive to user input by a user.

18. A non-transitory computer readable medium storing executable computer program instructions for providing personnel crisis communications management, the computer program instructions when executed causes one or more computing systems to:
receive a communication including additional information about an event;
determine that the event corresponds to an event record in an event database, the event record containing available information about the event;
supplement the available information about the event based on the additional information about the event;
identify a plurality of users associated with the event to whom additional information is available based on properties of the event and information about the plurality of users stored in the event database;
send a notification to a plurality of user devices associated with the plurality of users, the notification indicating the available information about the event has been supplemented;
provide, to a first user device that is associated with a first user of the plurality of users, first information about the event for presentation in a user interface of the first user device, the first information including the supplementary information and based on a permission level of the first user;
provide, to a second user device that is associated with a second user of the plurality of users, second information about the event for presentation in a user interface of the second user device, the second information including the supplementary information and based on a permission level of the second user;
receive status updates from a first subset of a plurality of user devices, each user device associated with a corresponding tracked user, and each status update including a status for the corresponding tracked user;
identify a second subset of the user devices from which recent status updates have not been received;
determine, for each of the second subset of the user devices, an inferred status for the corresponding tracked user, the inferred status based on previous status information associated with the corresponding tracked user;

aggregate the statuses and inferred statuses of the tracked users;

provide a dashboard display indicating the status of viewed users, the viewed users being a subset of the tracked users; and provide, for a third user, user interface controls for at least one of: viewing the status of a selected one of the viewed users in greater detail, filtering the viewed users based on status, filtering the viewed users based on location, filtering the viewed users based on assigned roles, and filtering the viewed users based on recency of status updates.

19. The non-transitory computer readable medium of claim 18, wherein the computer program instructions further comprise instructions that when executed causes the one or more computing systems to send an additional notification to a notification device associated with the event, the notification device being one of: a networked computer; a smart-phone; a tablet; an IP phone; a satellite phone; a landline phone; a mobile phone; a social network server configured to distribute the additional notification through via a social network; a speaker system; a display board; a TV system; a Land Mobile Radio; a Fire Alarm Control Panel; and a web site server configured to add the notification to a web site feed.

20. The non-transitory computer readable medium of claim 18, wherein the computer program instructions further comprise instructions that when executed causes the one or more computing systems to:

authenticate credentials of a device from which the communication was received;

validate the additional information within the communication; and acknowledge receipt of the communication to the device.

21. The non-transitory computer readable medium of claim 18, wherein the communication is received from an automated system and the computer program instructions further comprise instructions that when executed causes the one or more computing systems to:

authenticate credentials of the automated system; and validate content contained within the communication.

22. The non-transitory computer readable medium of claim 18, wherein the computer program instructions further comprise instructions that when executed causes the one or more computing systems to:

determine a security/sensitivity categorization for the event based on the available information; and store the security/sensitivity categorization in the event record.

23. The non-transitory computer readable medium of claim 18, wherein the permission level of the first user is based on at least one of: a security/sensitivity categorization; a type of the event; a role of the first user; a geographical location of the first user; a geographical location associated with the communication; characteristics of the first user device; and characteristics of a network to which the first user device is connected.

* * * * *